(12) United States Patent
Hunt et al.

(10) Patent No.: US 7,718,962 B2
(45) Date of Patent: May 18, 2010

(54) DEFECT IMAGING DEVICE AND METHOD

(75) Inventors: Alan W. Hunt, Pocatello, ID (US); J. Frank Harmon, Pocatello, ID (US); Douglas P. Wells, Pocatello, ID (US)

(73) Assignee: Idaho State University and the Board of Educa, Pocatello, ID (US)

( * ) Notice: Subject to any disclaimer, the term of this patent is extended or adjusted under 35 U.S.C. 154(b) by 289 days.

(21) Appl. No.: 11/807,568

(22) Filed: May 29, 2007

(65) Prior Publication Data

US 2008/0067372 A1 Mar. 20, 2008

Related U.S. Application Data

(60) Provisional application No. 60/810,883, filed on Jun. 5, 2006.

(51) Int. Cl.
*G21K 7/00* (2006.01)

(52) U.S. Cl. .................. 250/308; 250/306; 250/309; 250/363.01; 250/363.03; 250/363.04; 376/156; 376/157; 850/63

(58) Field of Classification Search .................. 250/306, 250/307, 309, 308, 363.01, 363.03, 363.04; 850/63; 376/156, 157
See application file for complete search history.

(56) References Cited

U.S. PATENT DOCUMENTS

| | | | | |
|---|---|---|---|---|
| 4,463,263 A | * | 7/1984 | Padawer ................. | 250/363.01 |
| 4,983,841 A | * | 1/1991 | Stewart et al. ........... | 250/358.1 |
| 5,200,619 A | * | 4/1993 | Asoka kumar et al. ...... | 250/307 |
| 5,262,651 A | * | 11/1993 | Bradshaw et al. ........ | 250/492.2 |
| 5,821,541 A | * | 10/1998 | Tumer ................... | 250/370.09 |
| 6,178,218 B1 | * | 1/2001 | Akers et al. .................. | 376/159 |
| 6,236,050 B1 | * | 5/2001 | Tumer ................... | 250/370.09 |
| 7,078,699 B2 | * | 7/2006 | Seppi ..................... | 250/358.1 |
| 2003/0043951 A1 | * | 3/2003 | Akers ........................ | 376/157 |
| 2003/0048864 A1 | * | 3/2003 | Akers ........................ | 376/157 |
| 2003/0227996 A1 | * | 12/2003 | Francke et al. ................. | 378/5 |
| 2004/0173745 A1 | * | 9/2004 | Uedono et al. ............. | 250/309 |
| 2004/0178353 A1 | * | 9/2004 | Perez et al. ................. | 250/427 |
| 2004/0227078 A1 | * | 11/2004 | Koguchi et al. ............. | 250/310 |
| 2005/0117682 A1 | * | 6/2005 | Akers ........................ | 376/157 |
| 2006/0013350 A1 | * | 1/2006 | Akers ........................ | 376/156 |
| 2006/0257315 A1 | * | 11/2006 | Magill et al. ............... | 424/1.11 |
| 2007/0029489 A1 | * | 2/2007 | Castellane et al. ..... | 250/363.01 |

\* cited by examiner

*Primary Examiner*—David A Vanore
*Assistant Examiner*—Michael J Logie
(74) *Attorney, Agent, or Firm*—Dale B Halling

(57) ABSTRACT

The present invention is directed to a defect imaging device that has an energy beam that is directed at a device under test. The energy beam creates positrons deep within the material of the device under test. When the positrons combine with electrons in the material they produce a pair of annihilation photons. The annihilation photons are detected. The Doppler broadening of the annihilation photons is used to determine if a defect is present in the material. Three dimensional images of the device under test are created by directing the energy beam at different portions of the device under test.

6 Claims, 4 Drawing Sheets

# DEFECT IMAGING DEVICE AND METHOD

RELATED APPLICATIONS

The present application claims priority on the provisional patent application entitled "Atomic Defect Imaging Techniques", filed Jun. 5, 2006 and having Application No. 60/810,883 and is hereby incorporated by reference.

STATEMENT REGARDING FEDERALLY SPONSORED RESEARCH

Not Applicable

THE NAMES OF THE PARTIES TO A JOINT RESEARCH AGREEMENT

Not Applicable

REFERENCE TO A SEQUENCE LISTING, A TABLE, OR A COMPUTER PROGRAM LISTING

Not Applicable

BACKGROUND OF THE INVENTION

The failure of structural and industrial materials costs the U.S. economy approximately $100 billion per year. Various non-destructive testing techniques have been employed over the years, one of them being Doppler broadening measurements using either slow positron beams or wide-energy spectrum positron beams originated from radioactive sources. However, the thickness of the samples under investigation by these methods is severely limited by the range of the impinging positrons inside the samples being tested, generally only tens of microns. In addition, the high cost and complexity of obtaining positron beams has limited the application of Doppler broadening spectroscopy techniques to basic materials science with little commercial or industrial application.

BRIEF SUMMARY OF INVENTION

The present invention is directed to a defect imaging device that overcomes these and other problems. The defect imaging device has an energy beam that is directed at a device under test. The energy beam creates positron deep within the material of the device under test. When the positrons combine with electrons in the material they produce a pair of annihilation photons. The annihilation photons are detected. The Doppler broadening of the annihilation photons is used to determine if a defect is present in the material. Three dimensional images of the device under test are created by directing the energy beam at different portions of the device under test.

DETAILED DESCRIPTION OF THE INVENTION

Figure 1:
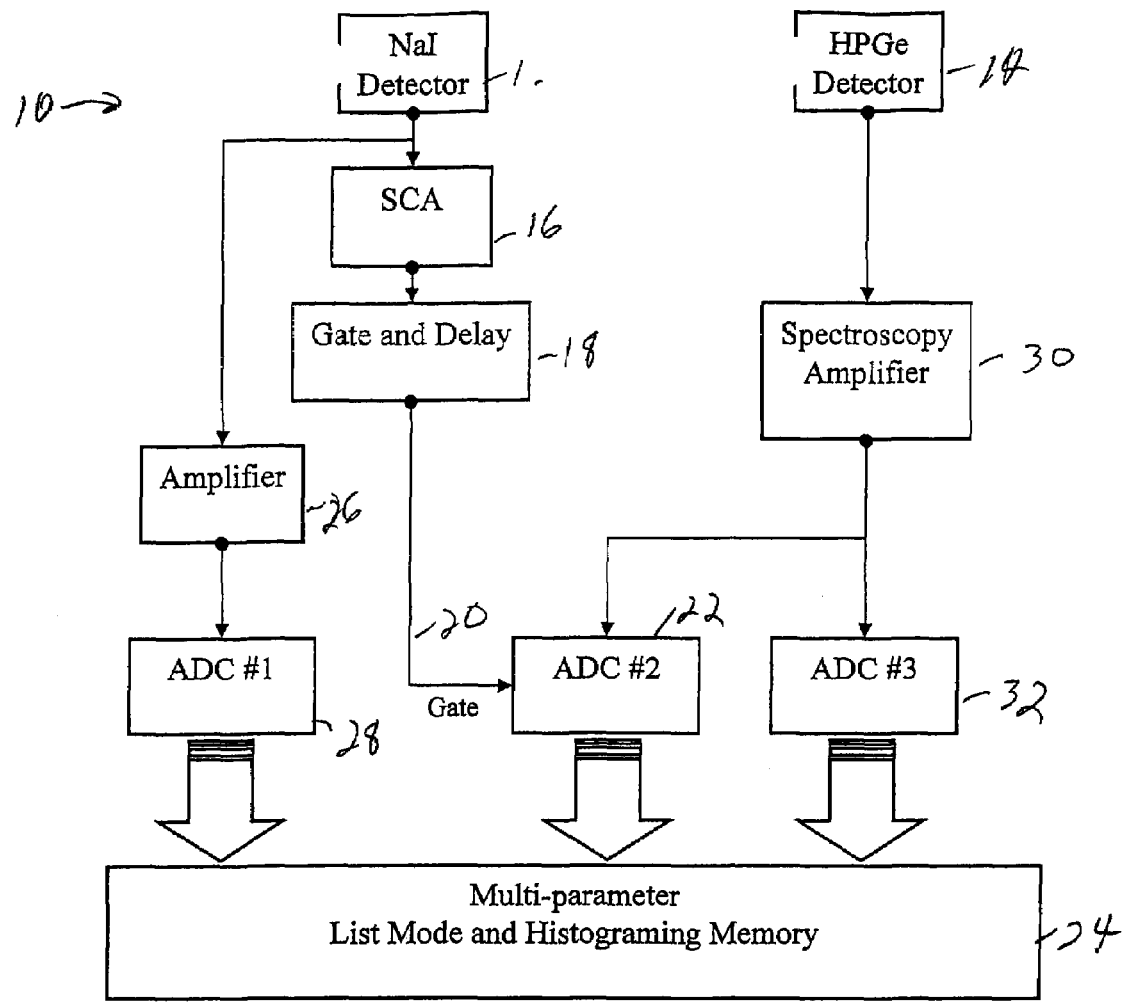
FIG. 1 is a block diagram of a defect imaging device in accordance with one embodiment of the invention.

The invention enables one to analyze any material for defects deep within the material, whether a result of manufacturing defects, stress, or otherwise, and to image the defects in two and three dimensions. The invention can be applied to static or dynamic objects and materials, does not create radiation above regulatory restrictions, and is portable and highly configurable so that it can be applied in a wide variety of manufacturing environments and to virtually any object or structure, wherever it may be located. The device described herein can be used to analyze defects in objects and structures, large and small, of any construction or composition; crystal, metal, alloy, polymer, welded, bonded, cast or formed.

The invention creates positrons deep within materials with photo-nuclear methods. Three methodologies are employed to do this. The first involves the use of a bremsstrahlung beam with a maximum energy above the neutron emission thresholds to produce residual nuclei in excited states. The second involves the use of a bremsstrahlung beam with a maximum energy above the electron-positron threshold, but below the neutron emission threshold. The third method involves the use of a proton beam. These three methods of producing positrons in materials are described in greater detail herein.

Using any these photo-nuclear methods the invention images and analyzes defects in any material, of any size or thickness, at the atomic and larger levels. As described herein, the invention is referred to as the "Defect Imaging Device" and the combination of methodologies and technologies employed in its use and operation are collectively referred to as "Pair Production-Positron Annihilation Spectroscopy" or "PP-PAS". As described in more detail below, the Defect Imaging Device employs PP-PAS to: (i) create positrons within a material to be tested through pair production or photo-activation by exposure to a bremsstrahlung (or proton-capture) gamma-beam originating from an electron or proton accelerator; (ii) recording the annihilation photons emitted from the test material during exposure by a high energy resolution detector; (iii) recording and analyzing the time frame and decay rate of annihilation photons so created; (iv) recording and analyzing the angular correlation of annihilation photons; and, (v) imaging the pattern and spectra of annihilation photons in two and three dimensions using Doppler broadened spectra of the annihilation photons.

The principal components of the Defect Imaging Device consist of: (i) a pulsed or continuous high energy electron accelerator of 2 MeV and above, incorporating an appropriate bremsstrahlung converter and collimators, or in the alternative, a pulsed or continuous proton accelerator; (ii) one or more shielded and collimated high energy resolution detectors of the energy spectrometer and time spectrometer type; (iii) electronic circuitry properly configured to capture and amplify the signal created by the detection of annihilation photons and to measure the Doppler broadened spectra of the annihilation photons; and, (iv) a computed tomography technology to image the results of the material analysis.

2a. Positron Creation; High Energy Electron Accelerator, Pulsed or Continuous.

The central component of the Defect Imaging Device and the underlying PP-PAS methodologies and technologies involves the application of high-energy electron accelerator technology, either pulsed or continuous at energies of 2 MeV and above to create positrons in a test material. Electron accelerators are well-established electrical devices that deliver directed beams of electrons. For this new application, a secondary beam of photon beams is produced by electron bremsstrahlung using an appropriate heavy metal bremsstrahlung converter. The resulting photon beam (the "source energy beam") is directed at the material to be tested. The source energy beam is collimated using one or more collimators depending upon the material to be tested so that the beam width and scan length are suitable to the test material's dimensions. In one configuration of the invention the source beam's maximum energy is above the neutron emission threshold required to produce residual nuclei in excited states. In a second configuration of the invention the source energy beam's maximum gamma energy is above the electron-positron pair production threshold but below the neutron emission threshold. In either configuration, the source energy beam produces electron-positron pairs ("pair production") in the test object. It is the production of positrons in the test material via these and the method described in 2b below that form the basis for the ability of the Defect Imaging Device to detect and image defects down to the atomic level in virtually any material of any size.

Another configuration of the Defect Imaging Device will also employ a continuous or pulsed laser beam, in conjunction with the Source Beams described above and in 2b below to induce stress in the test material.

2b. Alternative Positron Creation; Proton Accelerator, Pulsed or Continuous.

An alternative method of pair production within test materials is via proton-capture using a pulsed or continuous proton accelerator. This method is similar in application to that described in 2a above except that an appropriately collimated proton beam (the "source energy beam") is directed at the test material. This causes the creation of photons within the test material itself. These photons result in pair production as they pass through the test material.

2c. Detection of Annihilation Photons.

When subject to either of the source energy beams described in 2a and 2b above, positrons will be created within the test material via pair production. When a positron so created collides with an electron within the test material, both particles undergo annihilation, releasing radiation energy consisting of two 511 keV photons ("annihilation photons"). These annihilation photons are detected with high-energy resolution detectors, such as high purity germanium detectors, of both the energy spectrometer and time spectrometer type. These detectors are oriented to the test material and the source energy beam so as to minimize the possible detection of non-annihilation photon energy and are further shielded and collimated in a way to detect only emissions from the test material.

2d. Measurement and Analysis of Annihilation Photons; Doppler Broadening.

As the photon produced positrons travel within the test material they annihilate with electrons within the material producing two 511 keV annihilation photons. Because the distribution of electrons is uniform throughout a material, the production of annihilation photons will likewise be uniform throughout the material. However, a characteristic of "defect points" within any given material (at both the atomic and larger level) is that electrons in and about defect points will have low momentum vis-à-vis electrons in those portions of the material without defects. These defects include mono-vacancies, di-vacancies and larger open volume defects in the material. The annihilation of positrons with high momentum electrons in a test material as compared to low momentum electrons in the same test material results in Doppler broadening. Consequently, the annihilation of a positron in material containing one of these low momentum electrons (i.e. a defect) as compared to the annihilation of a positron with the high momentum electrons in the material (i.e. a non-defect) can be analyzed and imaged using the Doppler broadening techniques described herein. Thusly, the defect point(s) in the material are identified and imaged using the techniques described herein.

2e. Measurement and Analysis of Annihilation Photons; Timeframe.

The time period during which annihilation photons are produced and the rate of decay in production can be measured using the techniques described above and provide an important diagnostic tool respecting the nature of the material and any defects. In particular, the larger the defect the longer that the positron "lives" because the presence of defects means the absence of atoms and their associated electrons. Less electrons means less probability of a positron-electron collision and, therefore, a longer lifetime.

2f. Measurement and Analysis of Annihilation Photons; Angular Correlation.

The angle at which each two annihilation photons are emitted during the process of positron annihilation can be measured using the techniques described above and provide another important diagnostic tool respecting the nature of the material and any defects. When a positron annihilates with a high-momentum electron, there is a significant Doppler angular shift (away from 180 degrees), just like there is a significant Doppler energy shift (from 511 keV) in the presence of defects, the frequency of collisions with high-momentum electrons goes down, and the angular Doppler broadening decreases.

2g. Imaging of Annihilation Photons.

The detection of the annihilation photons by the detectors described in 2c above creates a signal that is amplified and processed using electronic circuitry. The signals so processed (including one or all of the Doppler broadening, timeframe, and angular correlation methodologies described in 2d, 2e, and 2f above) are then analyzed using computed tomography techniques to create an image of any defects in the material.

2h. Configuration of the Defect Imaging Device.

The Defect Imaging Device described herein employs the methodologies and technologies described herein to image defects occurring in materials in two and three dimensions. The application of the invention requires that the object to be tested be scanned by the source beam. While numerous configurations of the device will be employed depending upon the objects to be tested (for example, steel railroad rails versus small automotive parts) the configurations will be one of two general types.

The first general type is a Defect Imaging Device that is more or less stationary and in which the object to be tested is placed (or through which it passes) in order to be tested. In this configuration the object scanned is moved through the source beam in two or three dimensions using an appropriate combination of mechanical and beam orientation techniques so as the test site on the object is subjected to the source beam. The detectors are located in a fixed position with respect to the source beam and test object so as to maximize the capture of annihilation photons from the test object.

The second general type is a Defect Imaging Device that is mobile or portable and which is placed in the proper location with respect to, or moved around and about, the object to be tested. In this configuration, the object scanned remains more or less stationary. The source beam of the Defect Imaging Device scans the object in two or three dimensions using an appropriate combination of mechanical and beam orientation techniques so that the test site on the object is subjected to the source beam. The detectors are located in a fixed position with respect to the source beam and move about the test object in relation to the source beam.

FIG. 1 is a block diagram of the electronics used to image defects using positron annihilation spectroscopy. The system 10 has a sodium iodine (NaI) detector 12 and a high purity germanium (HPGe) detector 14. The sodium iodine (NaI) detector 12 is connected to a single channel analyzer 16. The single channel analyzer 16 determines if a signal is above a certain threshold. The output of the single channel analyzer 16 is coupled to a gate and delay electronics block 18. The gate and delay block 18 has a gate signal 20 that gates a data acquisition counter 22. The output of the data acquisition counter 22 is coupled to a computer 24 that runs a multi-parameter list mode and histogram program.

The sodium iodine (NaI) detector 12 is also coupled to an amplifier 26. The amplifier 26 is coupled to another data acquisition counter 28. The output of the data acquisition counter 28 is coupled to a computer 24 that runs a multi-parameter list mode and histogram program.

The high purity germanium (HPGe) detector 14 is coupled to a spectroscopy amplifier 30. The spectroscopy amplifier 30 is a highly linear amplifier that preserves the pulse shape from the high purity germanium (HPGe) detector 14. The output of the spectroscopy amplifier 30 is split into two parts. One part is coupled to the data acquisition counter 22 and the second part is coupled to another data acquisition counter 32.

Figure 2:
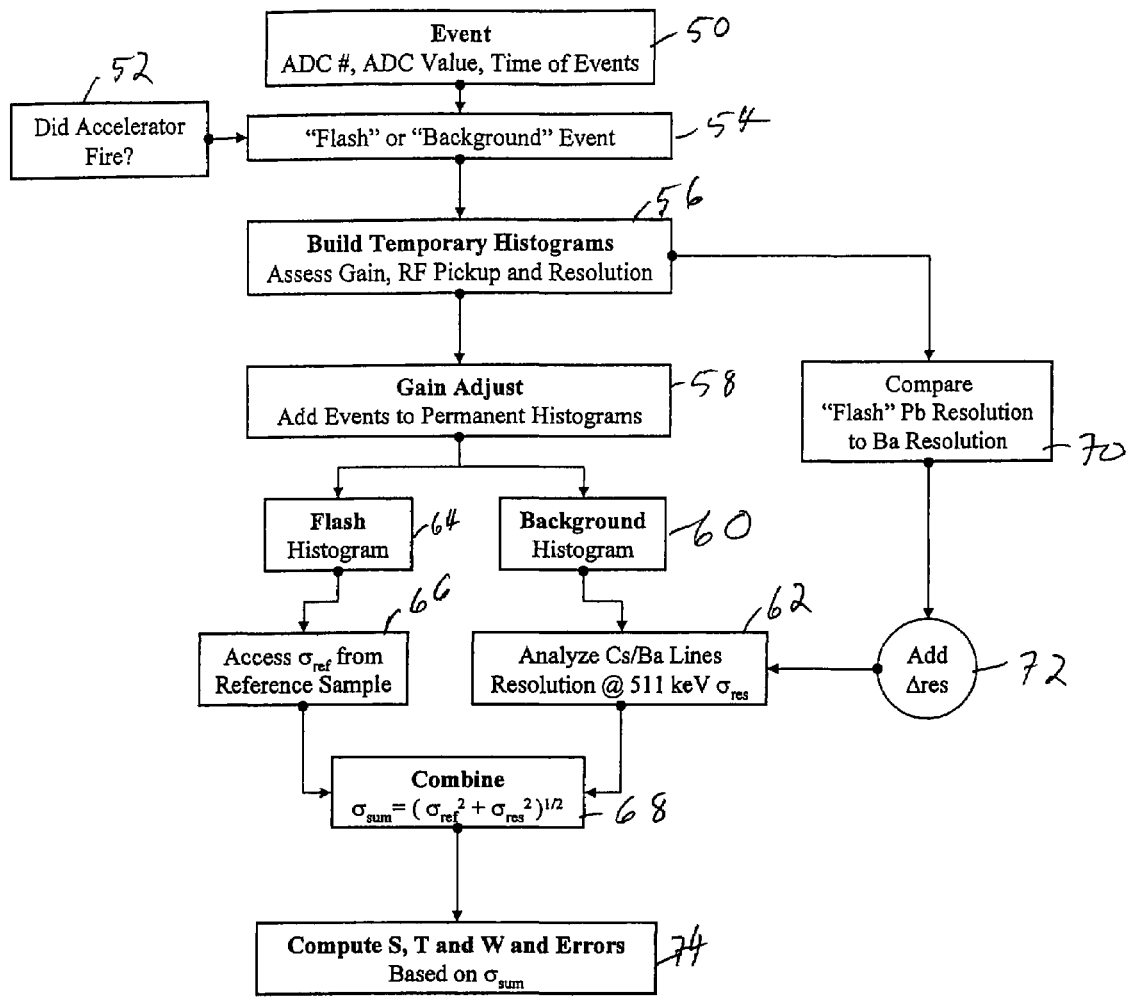
FIG. 2 is a flow chart of the steps used in a method of operating a defect imaging device in accordance with one embodiment of the invention.

FIG. 2 is a flow chart of the steps used to process the data gathered by the electronics in FIG. 1. The process starts, by logging an event data at step 50. The parameters collected include the data acquisition counter number (i.e., whether the data comes form ADC 22, 28 or 32), the ADC value or maximum amplitude and the time of the event. At step 52, it is determined if the accelerator fired. Based on this information, an event is determined to be either a flash or a background event at step 54. These steps 50, 52 & 54 are repeated for multiple events and the information is used to build temporary histograms at step 56. These histograms are used to assess the gain from the electronics and adjust the output for a standard gain profile. In addition the histograms are used to determine if there is any RF noise in the data and adjust the resolution accordingly. The gain adjustment starts by adding the temporary histograms to permanent histograms at step 58. Next, the process splits for background events and flash events (test data). If the histogram is a background event at step 60, then the cesium (Cs) and barium (Ba) lines in the histogram are analyzed and the resolution of the annihilation photons (511 keV) is adjusted accordingly at step 62. When the histogram is a flash histogram at step 64 the spreading of a reference sample is determined at step 66. The total energy spreading that can be expected is determined at step 68 and this information is used to determine if an event(s) shows a defect.

In order to determine if any RF noise is present in the data the resolution (energy spreading) of the lead lines are compared to the resolution of the barium lines at step 70. When there is a difference in the amount of spreading in these two groups of lines it is due to RF noise and this is added to the background information at step 72.

Once the histograms have been adjusted for spreading the S, T and W and Errors are computer at step 74 and the determination of material defects is made. The S parameter is the "Shape" parameter and reflects the annihilation with low momentum valence and unbound electrons and is defined as the ratio of the counts in the central region of the peak to the counts in the peak. The W parameter for "Wings" reflects the annihilation with high momentum core electrons and is defined as the ratio of counts in the wing regions of the peak to the total counts in the peak. A high concentration of defects, or an increase in the means size of defects, leads to a larger contribution of annihilation photons from low momentum electrons because positrons are trapped at defects. This is reflected in Doppler broadening measurements by an increase in S parameter and a decrease in W parameter. The T parameter is W/S as the T parameter increase it means there are fewer defects and as the T parameter decreases it means there are more defects.

Figure 3:
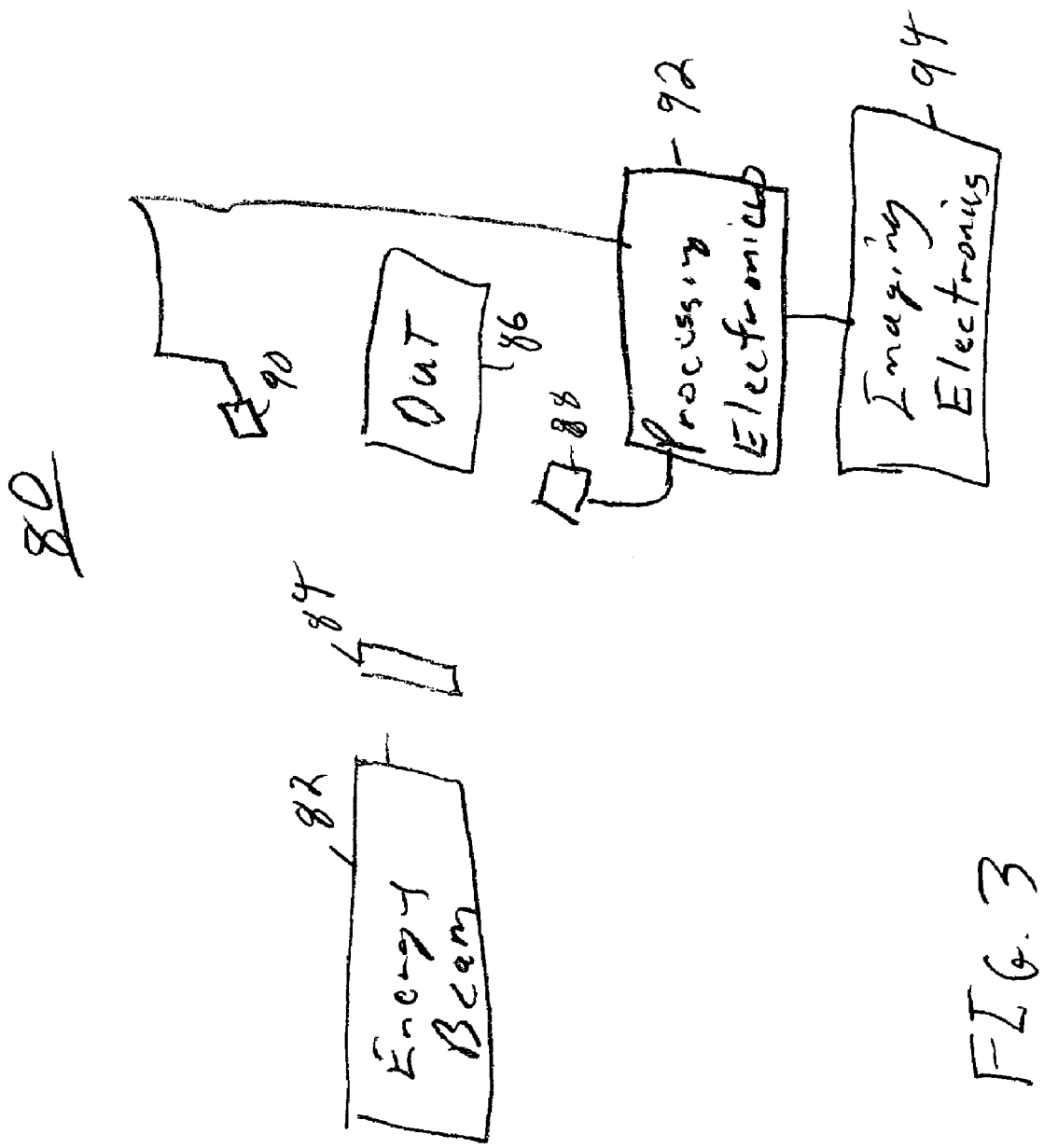
FIG. 3 is a block diagram of a defect imaging device in accordance with one embodiment of the invention.

FIG. 3 is a block diagram of a defect imaging device 80 in accordance with one embodiment of the invention. The device 80 has an energy beam 82 that has an output that passes through a collimator 84. The beam is then directed to a device under test 86. The annihilation photons are detected by detectors 88, 90. Processing electronics 92, such as that shown in FIG. 1, then determines the location of defects in the device under test 86. Imaging electronics 94 then combines a number of slices of the device under test 86 to form a two or three dimensional image of the defects in the device under test 86.

Figure 4:
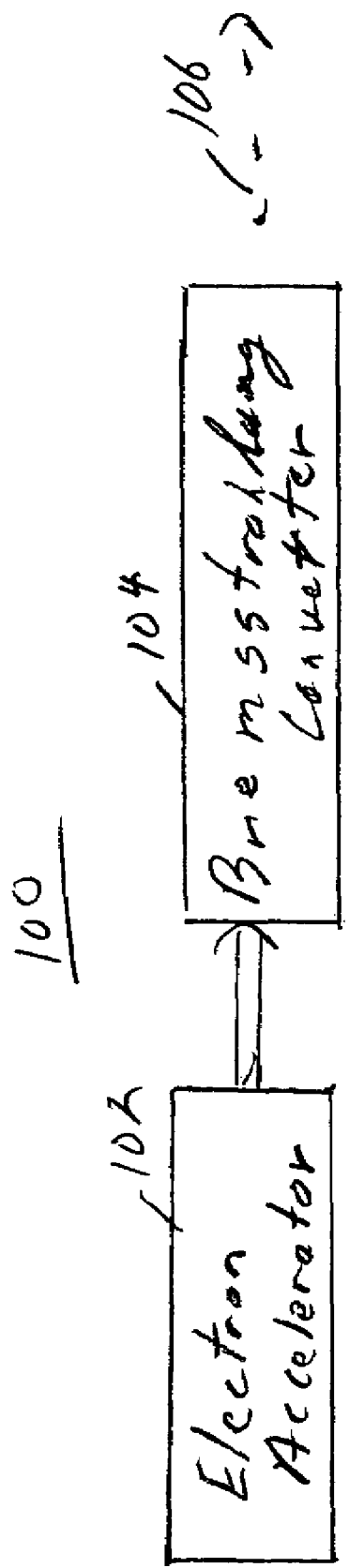
FIG. 4 is a block diagram of a energy beam system in accordance with one embodiment of the invention.

FIG. 4 is a block diagram of an energy beam system 100 in accordance with one embodiment of the invention. The energy beam system 100 has a electron accelerator 102 with an output 104 directed at a bremsstrahlung converter 104. The bremsstrahlung converter 104 converts the input electrons into gamma rays 106.

Figure 5:
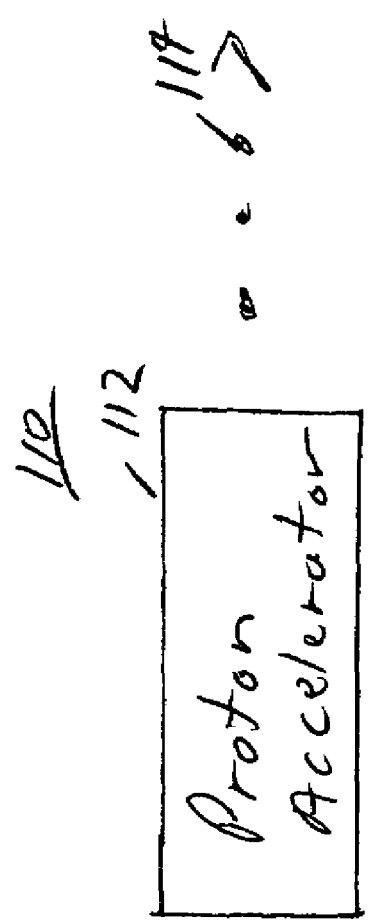
FIG. 5 is a block diagram of an energy beam system in accordance with one embodiment of the invention.

FIG. 5 is a block diagram of an energy beam system 110 in accordance with one embodiment of the invention, that uses a proton accelerator 112. The protons 114 are directed at the device under test.

Thus there has been describe a device for nondestructive defect analysis of virtually any material, including crystals, metals, alloys, and polymers. The method employed allows one to study defects in thick samples; up to meters in some materials. These are depths of study unavailable by any other known method of nondestructive analysis. The methods employed are commercially economical, can be performed on materials in-situ without removal to a specialized laboratory, can be performed on operating systems (for example, the turbine blades of an operating jet engine), on thick structures, and at radiation levels within regulatory requirements. This invention is the only method for nondestructive testing that is penetrating, portable, and that can reliably detect and image defects in thick structural and/or operating materials.

While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

What is claimed is:

1. A defect imaging device, comprising:
an energy beam system having an output of photons directed at a device under test and producing a positron instantaneously by electron-positron pair production in the device under test, wherein the output has a maximum energy above an electron-positron pair production threshold but below a neutron emission threshold;
a detector receiving an annihilation photon from the annihilation of the positron and determining a momentum of an electron forming an annihilation photon.

2. The device of claim 1, further including an imaging system receiving an electrical output from the detector.

3. The device of claim 1, wherein the energy beam system includes an electron accelerator having an output directed at a bremsstrahlung converter.

4. The device of claim 3, further including a collimator at an output of the bremsstrahlung converter.

5. The device of claim 1, wherein the detector is a high purity germanium detector.

6. The device of claim 5, further including a sodium iodide detector.

* * * * *